United States Patent [19]

Akkerboom et al.

[11] 4,422,971

[45] Dec. 27, 1983

[54] PROCESS FOR THE PREPARATION OF 6-AMINOPENICILLANIC ACID-1,1-DIOXIDE

[75] Inventors: Piet J. Akkerboom, RT Zoetermeer; Christophorus Oldenhof, TM Zoetermeer, both of Netherlands

[73] Assignee: Gist-Brocades N.V., Delft, Netherlands

[21] Appl. No.: 293,621

[22] PCT Filed: Dec. 10, 1980

[86] PCT No.: PCT/NL80/00039

§ 371 Date: Aug. 4, 1981

§ 102(e) Date: Aug. 4, 1981

[87] PCT Pub. No.: WO81/01707

PCT Pub. Date: Jun. 25, 1981

[30] Foreign Application Priority Data

Dec. 10, 1979 [NL] Netherlands ........................ 7908867

[51] Int. Cl.³ ................. C07D 499/04; C07D 499/42
[52] U.S. Cl. ............................ 260/245.2 R; 260/239.1

[58] Field of Search ...................... 260/245.2 R, 239.1

[56] References Cited

U.S. PATENT DOCUMENTS

| 3,528,965 | 9/1970 | Cole et al. | 260/245.2 |
| 3,663,563 | 5/1972 | Fosker et al. | 260/245.2 |
| 3,809,699 | 5/1974 | Ishimaru | 260/245.2 |
| 4,021,426 | 5/1977 | Oppici et al. | 260/245.2 R |
| 4,072,676 | 2/1978 | Sellsledt | 260/245.2 |
| 4,128,547 | 12/1978 | Van der drift et al. | 260/239.1 |
| 4,260,598 | 4/1981 | Barth | 424/114 |

Primary Examiner—Mary C. Lee
Attorney, Agent, or Firm—Hammond & Littell, Weissenberger and Muserlian

[57] ABSTRACT

A novel process for the preparation of 6-aminopenicilanic acid-1,1-dioxide and its non-toxic, pharmaceutically acceptable salts by deacylation of a penicillin-1,1-dioxide or its salts of which the 3-carboxylic acid is protected by such an easily removable group that a "one-pot process" is possible.

9 Claims, No Drawings

PROCESS FOR THE PREPARATION OF 6-AMINOPENICILLANIC ACID-1,1-DIOXIDE

The invention relates to a novel process for the preparation of 6-aminopenicillanic acid 1,1-dioxide, hereinafter called 6-APA-sulfone, and its salts.

European patent application publ. no. 0002927 describes the use of 6-APA-sulfone and its salts as agents for enhancing the antibacterial activity of β-lactam antibiotics, and its preparation by oxidation of 6-aminopenicillanic acid (6-APA) with a known sulfone generating oxidation agent such as potassium permanganate or 3-chloro-perbenzoic acid. However, the 6-amino group and the 3-carboxylic acid group have to be first protected with suitable groups which are removed after oxidation without affecting the ring structure of the molecule.

In Chemical Abstracts, volume 82 (1975), 156283Y, which corresponds to Japanese patent application Kokai No. 74 82,686, the preparation of 6β-aminopenicillanate 1-oxides is described by treating the methyl or trichloroethyl ester of a 6β-penicillin sulfoxide with an acid halide in an anhydrous solvent, reacting the intermediate with a lower alcohol and hydrolyzing the resulting imino ether with an acid.

In Chemical Abstracts, volume 80 (1974), 95941W, which corresponds to Japanese patent application Kokai No. 74 14,492, the preparation of 6-aminopenicillanic acid 1-oxide (6-APA sulfoxide) and its derivatives at the —COOH group is mentioned by treating 6-acylaminopenicillanic acid 1-oxide or its derivatives at the —COOH group with trialkyloxonium fluoroborate or an iminohalogenating agent and an organic hydroxyl compound or its alkali metal compound followed, if necessary, by hydrolyzing. However, in the examples only the methyl and trichloroethyl ester of benzylpenicillin acid 1-oxide in dichloromethane were treated with dimethylaniline and PCl$_5$.

Dutch patent application No. 7315579, which corresponds to Japanese patent application No. 72 115,113, describes the preparation of 6-APA sulfoxide derivatives by reacting benzyl or phenoxymethylpenicillanic acid 1-oxide derivatives with PCl$_5$ in the presence of a base, treating the resulting product with an alcohol and hydrolyzing the product obtained. Among the protecting ester groups mentioned in said patent application are alkyl groups, such as a methyl group, halogenating alkyl groups, such as a 2,2,2-trichloroethyl group, aralkyl groups, such as a benzyl group, a p-nitrobenzyl group, a p-methoxybenzyl group, a phenacyl and a benzhydryl group, trialkylsilyl groups such as a trimethylsilyl group, and the like, but in the examples only the use of 2,2,2-trichloroethyl and p-nitrobenzyl groups is demonstrated.

A disadvantage of the prior art methods which potentially may lead to the preparation of 6-APA sulfoxide itself is that the introduction and removal of protecting groups need at least two extra steps in the overall synthesis.

British Pat. Nos. 1,189,022 and 1,224,017 describe a method for preparing 6-aminopenicillanic acid by deacylating a 6-acylaminopenicillanic acid or a salt thereof by preparing a silyl ester of the 6-acylaminopenicillanic acid or a salt thereof, treating it with an agent which forms an imino bond, introducing an —OR group to the carbon atom which is involved in the formation of the imino bond whereby R is an alkyl or arylalkyl group, followed by splitting the imino bridge and the silyl ester group with agents containing a hydroxy group or with water.

After extensive research and experimentation it appeared impossible to isolate 6-APA-sulfoxide using the latter method, in which a 6-acylaminopenicillanic acid 1-oxide was used as the starting material instead of a 6-acylaminopenicillanic acid.

It could not be expected in any way that such a method should lead to reasonable results when used for penicillin sulfones. This appears also, for example, from the method of primary choice according to the aforementioned European patent application publ. No. 0002927 and from Dutch patent application Nos. 7305106 and 7508837, wherein 7-acylaminocephalosporanic acid 1-oxide derivatives are reduced to the corresponding 7-acylamidocephalosporanic acid derivatives with the aid of PCl$_5$. Besides, a person skilled in the art may derive from Chemical and Engineering News, Sept. 1979, page 33, left column, that compounds which effectively act as β-lactamase inhibiting agents must possess certain built-in structural properties. More particularly, an intact β-lactam ring, a good leaving group and a proton at the 6α position of an adequate acidity have to be present which properties lead said skilled person to expect a relatively unstable four-membered ring, which may be easily broken under the influence of the imino forming agents used.

It is an object of the invention to provide a simple, industrial process for the preparation of 6-APA-sulfone without the necessity for separate steps to protect the 6-amino and 3-carboxylic acid groups.

This and other objects and advantages of the invention will become obvious from the following detailed description.

The novel process of the invention for the preparation of 6-amino-penicillanic acid 1,1-dioxide and its non-toxic, pharmaceutically acceptable salts comprises subjecting a member of the group consisting of a penicillin-1,1-dioxide and its salts of which the 3-carboxylic acid group is protected by such an easily removable group that a "one-pot process" is possible, to deacylation to form 6-APA-sulfone and its salts.

In a preferred process of the invention, the 3-carboxylic acid group of the penicillin-1,1-dioxide or its salt is protected by a silyl group, the protected penicillin-1,1-dioxide is treated with an agent which forms an imino bond, an —OR group is introduced to the carbon atom which is involved in the formation of the imino bond, R being an alkyl or aralkyl group with 1 to 6 alkyl carbon atoms, the imino bridge is split with an agent containing a hydroxy group or with water, and the protective group is simultaneously removed from the 3-carboxylic acid group.

Suitable starting compounds for the method of the invention are penicillin-sulfones such as those described in U.S. Pat. Nos. 3,197,466 and 3,536,698, and by Guddal et al., Tetrahedron Letters, Vol. 9 (1962), p. 381 and J. Org. Chem., Vol. 28 (1963), p. 1927, preferably the 1,1-dioxides of benzyl- and phenoxymethylpenicillin.

The method of the invention has the great advantage with respect to the prior art in that raw materials are used as starting compounds and that these raw materials are easily obtained. For example, benzylpenicillin and its salts are prepared in large amounts by fermentation. Another suitable penicillin which may be obtained by fermentation is phenoxymethylpenicillin and its salts, and in general phenylalkyl and phenoxyalkyl penicillins and their salts may be used.

The said compounds may be oxidized in a simple way to the corresponding penicillin-sulfones as indicated above and no special measures need to be taken to protect possibly sensitive groups in the molecule. Only in the deacylation step is the protection of the 3-carboxylic acid group necessary, but for that purpose the easily manageable silylation is used. Silyl groups are easily removed during the deacylation as they are be split simultaneously with the splitting of the imino bridge with a compound containing a hydroxy group or with water.

With the term easily removable protecting groups are meant e.g. silicon, phosphorous or boron containing residues of which silicon containing residues are particularly preferred.

Suitable silylating agents include, for example, trialkylhalosilane such as trialkylchlorosilanes such as trimethylchlorosilane, dialkyldihalosilanes such as dialkyldichlorosilanes, and nitrogen containing silanes such as N,O-bistrimethylsilylacetamide, N,N'-bistrimethylsilylurea, hexamethyldisilazane or 3-trimethylsilyl-2-oxazolidinone.

The reaction between the penicillin-1,1-dioxide and the silylating agent, preferably dimethyldichlorosilane, is preferably carried out in an inert organic solvent under substantially anhydrous conditions. The reaction may be carried out at various temperatures, for example between 0° and 40° C., and goes smoothly at room temperature.

Then a reagent is added which forms an imino bond on the 6-amino nitrogen atom and examples of suitable reagents include iminohalogenating agents, such as $PCl_5$ and $POCl_3$ of which the former compound is preferred. The reaction is preferably carried out at lower temperatures. Suitable temperatures for the reaction are from about −60° to about 0° C., preferably from about −40° to about −10° C. To neutralize the acid formed in the reaction, an acid binding agent is added, for example, a tertiary amine such as pyridine, dimethylaniline or triethylamine. Preferably, dimethylaniline is used.

Examples of suitable alcohols to be used in the formation of the imino ether include aliphatic alcohols of 1 to 6 carbon atoms and benzyl alcohol. Preferably, an alcohol with 3 or 4 carbon atoms is used of which isobutanol is particularly preferred. The introduction of the —OR group may be preferably carried out at lower temperatures, for example from about −60° to about −10° C., preferably from about −50° to about −30° C. Preferably an acid binding agent is present also in this reaction such as a tertiary amine like pyridine, triethylamine or dimethylaniline.

The product formed may be easily hydrolyzed, insofar as this did not occur already through the addition of the alcohol and for that purpose, water may be added to the reaction mixture. The 6-APA-sulfone or its salt may be easily obtained by working up the reaction mixture.

In the following examples there are described several preferred embodiments to illustrate the invention. However, it is to be understood that the invention is not intended to be limited to the specific embodiments.

EXAMPLE 1

STEP A: Preparation of benzylpenicillin-1,1-dioxide

A solution of 106.5 g (675 mmol) of potassium permanganate and 39.75 ml of 85% phosphoric acid (density 1.70) in 2.7 l of water was added at 0° to −10° C. to a solution of 250 g (675 mmol) of the potassium salt of benzylpenicillin in 3.5 l of water while keeping the pH at a value between 6 and 7.5 with the aid of a solution of 10% phosphoric acid in water. After stirring for 75 minutes, the reaction mixture was filtered at 5° C. through Hy-flo and the precipitate was washed twice with 750 ml of ice water. The filtrate was extracted three times with 3.3 l of ethyl acetate at a pH of 3 and the extract was dried over $MgSO_4$ and concentrated to 400 ml during which a product crystallized. The crystalline mass was vacuum filtered and washed with an equal mixture of ethyl acetate and diethylether to obtain 170.8 g of benzylpenicillin-1,1-dioxide. Another 15 g of the product was obtained from the mother liquor for a total yield of 74%.

STEP B: 6-Aminopenicillanic acid-1,1-dioxide 34.4 ml (273 mmol) of N,N-dimethylaniline were added to a suspension of 39.1 g (107 mmol) of benzylpenicillin 1,1-dioxide in 330 ml of methylene chloride under a nitrogen atmosphere and 11.9 ml (97 mmol) of dimethyldichlorosilane were added dropwise at 20° C. to the solution. After stirring for 45 minutes, 24 g (113 mmol) of phosphorus pentachloride were added at −50° C. and after 2 hours of stirring at −30° C., the reaction mixture was cooled to −50° C. Then, 167 ml of isobutanol were added dropwise over about 5 minutes and after 1 hour of stirring at −35° C., the reaction mixture was poured into 200 ml of water. The mixture was ice-cooled and the pH was adjusted to a value of 3.3 with 8% ammonium hydroxide solution. After stirring for 30 minutes, the precipitate formed was collected by vacuum filtration and was washed twice with 25 ml of an ice-cold mixture of equal parts of acetone and water to obtain 17.8 g (67%) of 6-aminopenicillanic acid-1,1-dioxide (6-APA-sulfone).

STEP C: p-Toluenesulfonic acid salt of 6-APA-sulfone

A solution of 1.9 g of p-toluenesulfonic acid. $H_2O$ in 10 ml of acetone was added dropwise to a suspension of 2.48 g of 6-APA-sulfone in 20 ml of ethyl acetate and after stirring for 1 hour at room temperature, the precipitate was collected by vacuum filtration and was washed four times with 5 ml of ethyl acetate to obtain 3.65 g (87%) of the p-toluenesulfonic acid salt of 6-aminopenicillanic acid-1,1-sulfone.

EXAMPLE 2

4.8 ml (38.2 mmol) of dimethylaniline were added all at once to a suspension of 3.91 g (10.7 mmol) of benzylpenicillin-1,1-dioxide in 33 ml of dry methylene chloride under a nitrogen atmosphere at room temperature. To the resulting solution, 1.19 ml (9.7 mmol) of dimethyldichlorosilane were added dropwise at 20° C. and after stirring for 45 minutes at room temperature, the reaction mixture was cooled to −50° C. Then, 2.4 g (11.3 mmol) of phosphorous pentachloride were added all at once and after stirring for 2 hours at −35° C., the reaction mixture was cooled to 20° C. below the desired reaction temperature. Then, 16.7 ml (179.5 mmol) of isobutanol were added dropwise over 5 minutes and the mixture was stirred at −20°, −30° or −40° C. At various times, a sample of 1 ml was taken and this sample was taken up in 10 ml of water and the pH is brought to a value of 6 to 7 with 4N sodium hydroxide solution. Then, the volume was adjusted to 100 ml with a phosphate buffer of pH 6.8. The concentrations of 6-APAsulfone in the samples were determined with HPLC. Although the differences were not large, it was found that in the long run, the highest yield was obtained at the lowest temperature.

EXAMPLE 3

The procedure of Example 1 was repeated, but instead of isobutanol a corresponding amount of n-propanol was used and the yield was 55%.

EXAMPLE 4

The procedure of Example 1 was repeated, but instead of isobutanol a corresponding amount of methanol was used and the yield was 26%.

EXAMPLE 5

The procedure of Example 1 was repeated, but instead of benzylpenicillin-1,1-dioxide, a corresponding amount of phenoxymethyl penicillin-1,1-dioxide was used and the yield was 32%.

We claim:

1. A process for the preparation of 6-amino-penicillanic acid-1,1-dioxide comprising protecting the 3-carboxylic acid of a penicillin-1,1-dioxide with an easily removable silicon, phosphorus or boron containing residue, reacting the latter with an imino halogenating agent to form the corresponding 6-imino compound, reacting the latter with an alcohol of the formula R—OH wherein R is selected from the group consisting of alkyl of 1 to 6 carbon atoms and aralkyl with 1 to 6 alkyl carbon atoms to form the corresponding imino ether and hydrolyzing the latter to obtain 6-amino-penicillanic acid-1,1-dioxide.

2. The process of claim 1 wherein 6-amino-penicillanic acid-1,1-dioxide is reacted with a non-toxic, pharmaceutically acceptable acid to form the corresponding acid addition salt.

3. The method of claim 1 wherein the 3-carboxylic acid group is protected by silylation.

4. The method of claim 3 wherein the silylation is carried out with a member of the group consisting of trialkylhalosilane, a dialkyldihalosilane and a nitrogen containing silane.

5. The method of claim 4 wherein the silylation is carried out with dimethyldichlorosilane.

6. The method of claim 1 wherein the agent used in the formation of an imino bond is $PCl_5$.

7. The method of claim 6 wherein the reaction with $PCl_5$ is carried out at a temperature from about $-40°$ to about $-10°$ C.

8. The method of claim 1 wherein the alcohol is isobutanol.

9. The method of claim 1 wherein the reaction with the alcohol is carried out at a temperature of from about $-50°$ to about $-30°$ C.

* * * * *